United States Patent

Griffith et al.

Patent Number: 5,912,286
Date of Patent: Jun. 15, 1999

[54] SILICONE-CONTAINING FLUOROPOLYMERS FOR CONTROLLED RELEASE OF ORGANIC LEACHANTS

[75] Inventors: James R. Griffith, Lanham; Stephen L. Snyder, Clinton, both of Md.

[73] Assignee: The United States of America as represented by the Secretary of the Navy, Washington, D.C.

[21] Appl. No.: 08/921,054

[22] Filed: Aug. 29, 1997

[51] Int. Cl.[6] .................................................. C08J 5/46
[52] U.S. Cl. ............................. 524/83; 524/84; 524/95; 524/111; 528/27; 528/38
[58] Field of Search ................. 528/27, 38; 524/84, 524/83, 95, 111

[56] References Cited

U.S. PATENT DOCUMENTS

| | | | |
|---|---|---|---|
| 4,127,687 | 11/1978 | Dupont | 428/35 |
| 4,898,895 | 2/1990 | Masuoka et al. | 523/122 |
| 5,597,584 | 1/1997 | Bhatt | 424/486 |

OTHER PUBLICATIONS

Griffith, J.R. and O'Rear, J.G., "Silicone Amine Cured Fluoroepoxy Resins" in Resins for Aerospace, May, C.A., ed., ACS Symposium Series, Washington DC, 1980, pp. 35–38.

Griffith, J.R., "Epoxy Resins Containing Fluorine", CHEMTECH 1982, 5, pp. 290–293.

Primary Examiner—Melvyn I. Marquis
Assistant Examiner—Caixia Lu Rutt
Attorney, Agent, or Firm—Thomas McDonell; Ralph T. Webb

[57] ABSTRACT

A composition comprises a leachable organic compound distributed throughout a polymer matrix formed by reacting a fluoroepoxy compound of the formula:

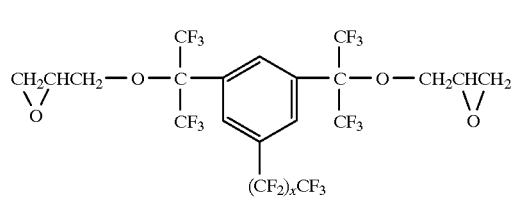

wherein x is an integer from 0 to 12, with a silicone amine curing agent of the formula:

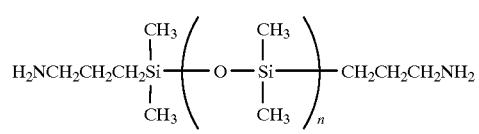

where n is the average degree of polymerization of the silicone amine curing agent and is 1 or greater. The leaching rate of the leachable organic compound is controlled by selecting the value of x in the fluoroepoxy compound and the value of n in the silicone amine curing agent. The composition may be used as a coating for protecting underwater substrates from fouling by marine organisms.

22 Claims, No Drawings

SILICONE-CONTAINING FLUOROPOLYMERS FOR CONTROLLED RELEASE OF ORGANIC LEACHANTS

BACKGROUND OF THE INVENTION

1. Field of the Invention

The invention relates generally to compositions having a leachable organic compound distributed throughout a polymer matrix and to methods of controlling the leaching rate of the leachable organic compound from the polymer matrix. In particular, the invention relates to compositions having a leachable organic compound distributed throughout a fluoroepoxy-silicone amine polymer matrix.

2. Description of the Related Art

Coating compositions containing leachable biocides are used to protect surfaces in an aquatic environment from fouling from marine organisms. Antifouling coating compositions containing biocides are disclosed in U.S. Pat. No. 4,127,687 to Dupont, in U.S. Pat. No. 4,898,895 to Masuoka et al, and in U.S. patent application Ser. No. 08/251419, filed May 31, 1994, by the present inventors. With antifouling coating compositions, it is important that the biocide leach out of the coating at a fast enough rate to provide a concentration of the biocide on the coated surface sufficient to protect the surface against fouling by marine organisms. On the other hand, if the leaching rate is too fast, the biocide may leach out of the coating completely in a short period of time, after which the coating is ineffective and must be replaced. U.S. Pat. No. 4,127,687 and U.S. patent application Ser. No. 08/251419, filed May 31, 1994, teach that the rate of leaching can be controlled by selecting a biocide with the appropriate degree of solubility to achieve the desired leaching rate. However, this method of controlling the leaching rate restricts the choice of biocide to those that meet the solubility criteria. It would be helpful to have an antifouling coating composition wherein the rate of leaching of any biocide can be controlled by altering the polymer matrix.

U.S. Pat. No. 4,898,895 describes an antifouling paint comprising an antifoulant and a vinyl polymer or copolymer containing a trimethylsilyl group or a polydimethylsiloxane and states that the polymer or copolymer controls the antifoulant so that it does not dissolve in seawater either excessively or insufficiently. However, the patent does not disclose any method of achieving precise control over the leaching rate.

Controlled release matrices for the release of organic compounds are also found in other fields such as the medical field, where it is often desirable to provide for the controlled release of a drug into the bloodstream or body tissues. For example, U.S. Pat. No. 5,597,584 discloses a method of controlling the rate of release of a drug from a silicone rubber matrix by changing the crosslink density of the silicone rubber matrix.

SUMMARY OF THE INVENTION

It is an object of the invention to provide a composition having a leachable organic compound distributed throughout a polymer matrix wherein the rate of leaching of the organic compound from the matrix can be controlled.

It is a further object of the invention to provide a coating composition and method for protecting a substrate from fouling by organisms by providing a composition having a biocide distributed throughout a polymer matrix wherein the rate of leaching of the biocide from the matrix can be controlled.

It is a further object of the invention to provide a coating composition and method for protecting a substrate from fouling by organisms by providing a composition having a biocide distributed throughout a polymer matrix wherein the rate of leaching of the biocide from the matrix is selected to provide effective long-term protection of the substrate.

These and other objects are attained by providing a composition comprising a polymer matrix and a leachable organic compound distributed throughout the polymer matrix, wherein the polymer matrix comprises the reaction product formed by reacting a fluoroepoxy compound of the formula:

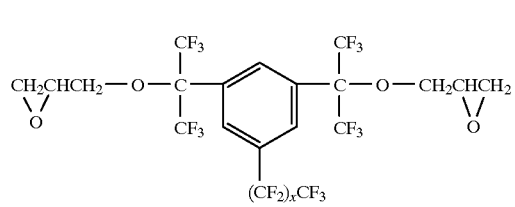

wherein x is an integer from 0 to 12, with a silicone amine curing agent of the formula:

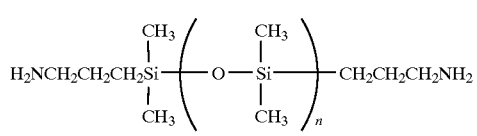

where n is the average degree of polymerization of the silicone amine curing agent and is 1 or greater. The rate of leaching of the organic compound from the polymer matrix can be controlled by controlling the relative amount of fluorocarbon and siloxane in the polymer matrix by selecting the value for x in the fluoroepoxy compound and the value of n in the silicone amine curing agent.

DETAILED DESCRIPTION OF THE PREFERRED EMBODIMENT

The invention relates to composition comprising a leachable organic compound distributed throughout a polymer matrix formed by reacting a fluoroepoxy compound of the formula:

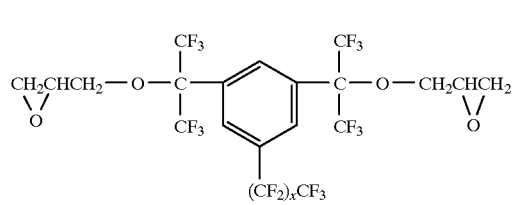

wherein x is an integer from 0 to 12, with a silicone amine curing agent of the formula:

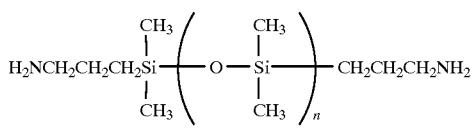

where n is the average degree of polymerization of the silicone amine curing agent and is 1 or greater. The leachable organic compound preferably comprises from about 0.5 to about 25% and more preferably from about 1 to about 20% by weight of the composition. The composition may be used in a variety of practical applications where it is desired to control the leaching rate of an organic compound from a matrix. Examples include the use of the composition for the controlled release of a drug into the bloodstream or body tissues or the use of the composition as a coating on surfaces of swimming pools, bathroom fixtures and similar items for the slow release of an antiseptic. As described below, the composition is especially useful as a coating for the controlled sustained release of a biocide to protect surfaces in an aquatic environment from fouling from aquatic organisms.

The fluoroepoxy compounds of formula 1 may be synthesized by conventional techniques. Methods for synthesizing these compounds are described in U.S. Pat. No. 3,879,430, incorporated herein by reference. In making the polymer matrix of the present invention, either a single compound of formula 1 or a mixture of compounds of formula 1 having a range of lengths of the fluorocarbon substituent (a range of values of x in formula 1) may be used.

The silicone amine curing agents of formula 2 (also called 3-aminopropyl terminated polydimethylsiloxanes) may also be synthesized by conventional techniques and are commercially available from various chemical companies including Gelest Inc, Tullytown, Pa., United Chemical Technologies, Inc, Bristol Pa. and Goldschmidt Chemical Corp., Hopewell, Va. The commercially obtained silicone amine curing agents are typically identified by their average molecular weight, which can be readily converted mathematically into the average degree of polymerization.

The selection of a particular fluoroepoxy compound and a particular silicone amine curing agent, that is, the selection of particular values for x and n in the above formulas 1 and 2 is made to control the relative amount of siloxane and fluorocarbon in the polymer and to control the leaching rate of the leachable organic compound from the polymer. A greater relative amount of fluorocarbon slows the leaching rate and a greater relative amount of siloxane speeds up the leaching rate.

The selection of the leachable organic compound depends upon the intended purpose of the composition. For drug delivery, the leachable organic compound can be any organic drug or active agent such as is described in U.S. Pat. No. 5,597,584, incorporated herein by reference. For the disinfection of surfaces such as the walls of swimming pools and bathroom fixtures, the leachable organic compound can be an organic antiseptic or disinfectant. If the composition is to be used as an antifouling coating for protecting a substrate in an underwater medium, the leachable organic compound can be any organic biocide. Examples of biocides are described in U.S. Pat. No. 4,127,687 to Dupont, in U.S. Pat. No. 4,898,895 to Masuoka et al, and in U.S. patent application Ser. No. 08/251419, filed May 31, 1994, by the present inventors, incorporated herein by reference. Preferably, the leachable organic compound is a 3-isothiazolone such as 4,5-dichloro-2-cyclohexyl-3-isothiazolone,
4,5-dichloro-2-n-hexyl-3-isothiazolone,
4,5-dichloro-2-n-octyl-3-isothiazolone,
4,5-dichloro-2-n-vinyl-3-isothiazolone,
4,5-dichloro-2-(4'-chlorobenzyl)-3-isothiazolone,
4-methyl-5-chloro-2-(4'-chloro phenyl)-3-isothiazolone,
5-chloro-2-(4'-chlorobenzyl)-3-isothiazolone,
5-chloro-2-(2'-phenylethyl)-3-isothiazolone,
4,5-dichloro-2-(2'-phenylethyl)-3-isothiazolone,
4-methyl-5-chloro-2-(3', 4'-diethylbenzyl)-3-isothiazolone, and mixtures thereof.

When the composition of the present invention is used as a coating composition for protecting a substrate in an underwater medium from fouling by organisms, the leachable organic compound is preferably 4,5-dichloro-2-n-octyl-3-isothiazolone, a biocide sold by Rohm & Haas Company, Philadelphia, Pa. under the tradename "C-9211" or "SEA-NINE", and the polymer matrix is preferably the reaction product of a fluoroepoxy compound of formula 1 where x is 7 and a silicone amine curing agent of formula 2 wherein n is about 11. Preferably, the 4,5-dichloro-2-n-octyl-3-isothiazolone comprises from from about 0.5 to about 25% and more preferably from about 1 to about 20% of the coating composition by weight.

In making the composition of the present invention, the leachable organic compound is first blended with the fluoroepoxy resin, and then the silicone amine curing agent is added to the mixture. The fluoroepoxy resin is heated to about 50°–60 ° C. and stirred while the leachable organic compound is added. The leachable organic compound should be added in a sufficient amount to accomplish the intended purpose. For example, if the composition is to be used as an antifouling coating for protecting a substrate in an underwater medium, the amount of biocide added should be enough to dissuade marine organisms from attaching themselves to the substrate. The amount of the biocide can be in the range of 0.5–25%, typically about 1–20%, based on the weight of the composition. After the fluoroepoxy resin and the leachable organic compound are mixed, the mixture is allowed to cool and then is heated to about 50°–60 ° C. and stirred again while the silicone amine curing agent is added. The silicone amine curing agent is preferably added in a stoichiometric amount with respect to the fluoroepoxy resin. Since the fluoroepoxy resin is difunctional and the silicone amine curing agent is tetrafunctional, one mole of the silicone amine curing agent should be added for every two moles of the fluoroepoxy resin. After the silicone amine curing agent is added, the mixture begins to cure to form the polymer matrix having the leachable organic compound distributed throughout the matrix. Before the mixture is completely cured, it may be applied to a substrate to form a coating. The curing of fluoroepoxy resins with silicone amine curing agents is described generally in Griffith, J. R. and O'Rear, J. G., "Silicone Amine Cured Fluoroepoxy Resins" in Resins for Aerospace, May, C. A., ed., ACS Symposium Series, Washington D.C., 1980, pp 35–38 and in Griffith, J. R., "Epoxy Resins Containing Fluorine", CHEMTECH 1982, 5, pp 290–293, the disclosures of which are incorporated herein by reference.

Having described the invention, the following examples are given to illustrate specific applications of the invention, including the best mode now known to perform the invention. These specific examples are not intended to limit the scope of the invention described in this application.

EXAMPLES

Example 1

A coating composition comprising a fluoroepoxy resin designated as "C-8" (the fluoroepoxy resin of formula 1 above wherein x is 7), a 1000 mw silicone amine (a mixture of silicone amine curing agents of formula 2 above wherein n has an average value of about 11, obtained from Goldschmidt Chemical Corp., Hopewell, Va. and designated "Tegomer 1000") and a biocide designated as "C-9211" (4,5-dichloro-2-n-octyl-3-isothiazolone) from Rohm and Haas Company was made as follows:

The fluoroepoxy resin was heated to about 50°–60 ° C. and the biocide was added with stirring to the hot fluoroepoxy resin liquid. The biocide was added in an amount so that it would constitute 6.5% by weight of the coating composition. The mixture was allowed to cool and then was reheated to about 50°–60 ° C. and stirred while the silicone amine curing agent was added. The silicone amine curing agent was added in the amount of about 2 parts by weight of fluoroepoxy resin to about 1 part by weight of the silicone amine curing agent. The mixture was allowed to cool into an almost transparent resin and was painted on to an epoxy test panel. The test panel was placed in the Chesapeake Bay during a summer and at the end of the season, the panel was found to be free of fouling organisms, whereas control panels were totally fouled.

Example 2

A series of sample coating compositions were made by the process described above and were coated onto test rods for determining the leaching rate of C-9211 biocide as a function of the silicone/fluorocarbon ratio. In each set, the molar ratio of the epoxy or fluoroepoxy compound to the silicon amine curing agent was 2 to 1. The sample coating compositions were as follows:

Set 1 (control): C-8 fluoroepoxy and 1000. mw silicone amine curing agent. No biocide was added.

Set 2: C-mix (a mixture of fluoroepoxies of formula 1 wherein x is from about 4 to about 11.), Si-2 (the silicone amine curing agent of formula 2 wherein n is 1), and 10% by weight of C-9211 biocide.

Set 3: Resorcinol diglycidyl ether (a compound similar to the fluoroepoxy resin, but having no 3 fluorocarbon content), Tegomer 1000 mw silicone amine and 10% by weight of C-9211 biocide.

Set 4: C-8 fluoroepoxy, Tegomer 1000 mw silicone amine and 10% by weight of C-9211.

It is anticipated that Set 3, which has the highest siloxane to fluorocarbon ratio (infinite), would have the highest leaching rate, that Set 2, which has the lowest siloxane to fluorocarbon ratio, would have the lowest leaching rate, and that Set 4, with an intermediate siloxane to fluorocarbon ratio, would have an intermediate leaching rate.

Obviously, many modifications and variations of the present invention are possible in light of the above teachings. It is therefore to be understood that, within the scope of the appended claims, the invention may be practiced otherwise than as specifically described.

What is claimed is:

1. A composition comprising a polymer matrix and a leachable organic compound distributed throughout the polymer matrix, wherein the polymer matrix comprises the reaction product formed by reacting a fluoroepoxy compound of the formula:

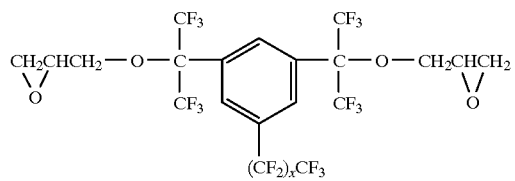

wherein x is an integer from 0 to 12, with a silicone amine curing agent of the formula:

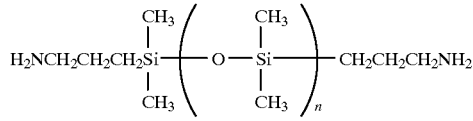

where n is the average degree of polymerization of the silicone amine curing agent and is 1 or greater.

2. The composition of claim 1, wherein the leachable organic compound comprises from about 0.5 to about 25% by weight of the composition.

3. The composition of claim 1, wherein the leachable organic compound comprises from about 1 to about 20% by weight of the composition.

4. The composition of claim 1, wherein the leachable organic compound is a biocide.

5. The composition of claim 1, wherein the leachable organic compound is a 3-isothiazolone compound.

6. The composition of claim 1, wherein the leachable organic compound is selected from the group consisting of 4,5-dichloro-2-cyclohexyl-3-isothiazolone, 4,5-dichloro-2-n-hexyl-3-isothiazolone, 4,5-dichloro-2-n-octyl-3-isothiazolone, 4,5-dichloro-2-n-vinyl-3-isothiazolone, 4,5-dichloro-2-(4'-chlorobenzyl)-3-isothiazolone, 4-methyl-5-chloro-2-(4'-chlorophenyl)-3-isothiazolone, 5-chloro-2-(4'-chlorobenzyl)-3-isothiazolone, 5-chloro- 2-(2'-phenylethyl)- 3-isothiazolone, 4,5-dichloro-2-(2'-phenylethyl)-3-isothiozolone, 4-methyl-5-chloro-2-(3', 4'-diethylbenzyl)-3-isothiazolone, and mixtures thereof.

7. The composition of claim 1, wherein the leachable organic compound is 4,5-dichloro-2-n-octyl-3-isothiazolone.

8. A method of making a composition comprising a polymer matrix and a leachable organic compound distributed throughout the polymer matrix, the composition having the property that when the composition is placed in a liquid medium, the leachable organic compound leaches from the polymer matrix at a predetermined selectable rate, the method comprising the steps of, combining a leachable organic compound with a fluoroepoxy compound of the formula:

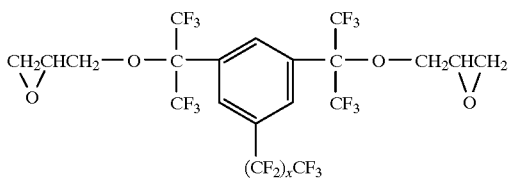

wherein x is an integer from 0 to 12, and a silicone amine curing agent of the formula:

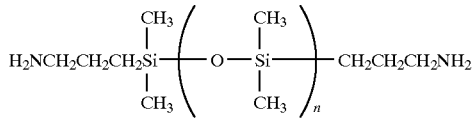

where n is the average degree of polymerization of the silicone amine curing agent and is 1 or greater,
    allowing the fluoroepoxy compound to react with the silicone amine curing agent to form a polymer matrix having the leachable organic compound distributed throughout the polymer matrix,
    wherein the predetermined selectable rate of leaching of the leachable organic compound is controlled by selecting the value of x in the fluoroepoxy compound and the value of n in the silicone amine curing agent.

9. A coating composition for protecting a substrate in an underwater medium from fouling by organisms comprising
    a polymer matrix and a leachable biocide distributed throughout the polymer matrix,
    wherein the polymer matrix comprises the reaction product formed by reacting a fluoroepoxy compound of the formula:

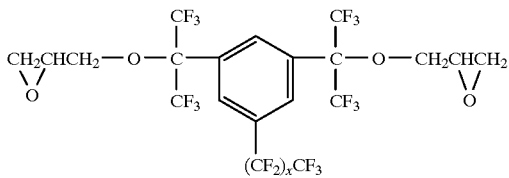

wherein x is an integer from 0 to 12, with a silicone amine curing agent of the formula:

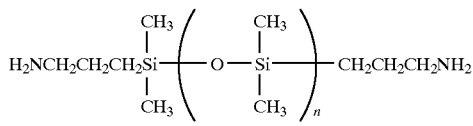

where n is the average degree of polymerization of the silicone amine curing agent and is 1 or greater,
    wherein the value of x in the fluoroepoxy compound and the value of n in the silicone amine curing agent are selected to provide a polymer matrix that allows an effective amount of the leachable biocide for protecting a substrate in an underwater medium from fouling by organisms to leach from the polymer matrix into the underwater medium.

10. The composition of claim 9 wherein the leachable biocide comprises from about 0.5 to about 25% by weight of the composition.

11. The composition of claim 9 wherein the leachable biocide comprises from about 1 to about 20% by weight of the composition.

12. The composition of claim 9 wherein the leachable biocide is a 3-isothiazolone compound.

13. The composition of claim 9 wherein the leachable biocide is selected from the group consisting of
    4,5-dichloro-2-cyclohexyl-3-isothiazolone,
    4,5-dichloro-2-n-hexyl-3-isothiazolone,
    4,5-dichloro-2-n-octyl-3-isothiazolone,
    4,5-dichloro-2-n-vinyl-3-isothiazolone,
    4,5-dichloro-2-(4'-chlorobenzyl)-3-isothiazolone,
    4-methyl-5-chloro-2-(4'-chlorophenyl)-3-isothiazolone,
    5-chloro-2-(4'-chlorobenzyl)-3-isothiazolone,
    5-chloro-2-(2'-phenylethyl)-3-isothiazolone,
    4,5-dichloro-2-(2'-phenylethyl)-3-isothiozolone,
    4-methyl-5-chloro-2-(3', 4'-diethylbenzyl)-3-isothiazolone, and mixtures thereof.

14. The composition of claim 9 wherein the leachable biocide is 4,5-dichloro-2-n-octyl-3-isothiazolone.

15. A coating composition for protecting a substrate in an underwater medium from fouling by organisms comprising
    a polymer matrix and a leachable biocide distributed throughout the polymer matrix,
    wherein the leachable biocide is 4,5-dichloro-2-n-octyl-3-isothiazolone and comprises about 1 to about 20% of the coating composition by weight, and
    the polymer matrix comprises the reaction product formed by reacting a fluoroepoxy compound of the formula:

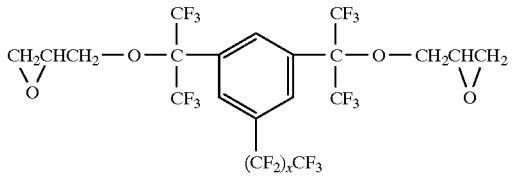

wherein x is 7, with a silicone amine curing agent of the formula:

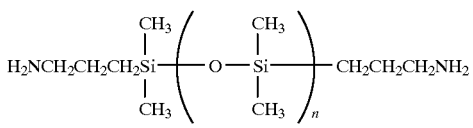

where n is the average degree of polymerization of the silicone amine curing agent and is about 11.

16. An article comprising a substrate and a coating composition disposed on the substrate, the coating composition comprising a polymer matrix and a leachable organic compound distributed throughout the polymer matrix,
    wherein the polymer matrix comprises the reaction product formed by reacting a fluoroepoxy compound of the formula:

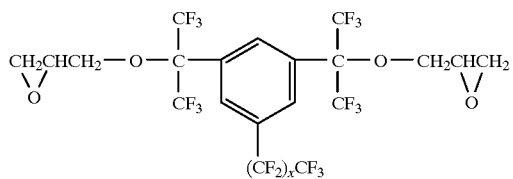

(CF$_2$)$_x$CF$_3$ wherein x is an integer from 0 to 12, with a silicone amine curing agent of the formula:

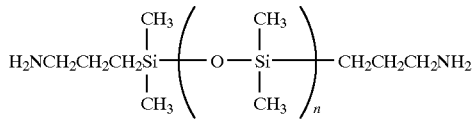

where n is the average degree of polymerization of the silicone amine curing agent and is 1 or greater.

17. A method of protecting a substrate in an underwater medium from fouling by organisms comprising the step of forming on the surface of the substrate a coating composition comprising a polymer matrix and a leachable biocide distributed throughout the polymer matrix, wherein the polymer matrix comprises the reaction product formed by reacting a fluoroepoxy compound of the formula:

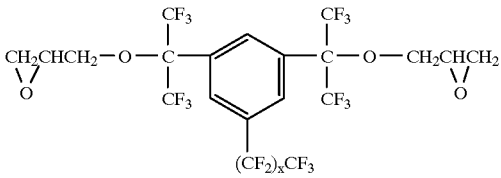

(CF$_2$)$_x$CF$_3$ wherein x is an integer from 0 to 12, with a silicone amine curing agent of the formula:

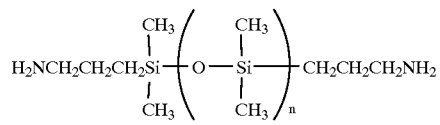

where n is the average degree of polymerization of the silicone amine curing agent and is 1 or greater, wherein the value of x in the fluoroepoxy compound and the value of n in the silicone amine curing agent are selected to provide a polymer matrix that allows an effective amount of the leachable biocide for protecting a substrate in an underwater medium from fouling by organisms to leach from the polymer matrix into the underwater medium.

18. The method of claim 17 wherein the leachable biocide comprises from about 0.5 to about 25% by weight of the composition.

19. The method of claim 17 wherein the leachable biocide comprises from about 1 to about 25% by weight of the composition.

20. The method of claim 17 wherein the leachable biocide is a 3-isothiazolone compound.

21. The method of claim 17 wherein the leachable biocide is selected from the group consisting of 4,5-dichloro-2-cyclohexyl-3-isothiazolone,
4,5-dichloro-2-n-hexyl-3-isothiazolone,
4,5-dichloro-2-n-octyl-3-isothiazolone,
4,5-dichloro-2-n-vinyl-3-isothiazolone,
4,5-dichloro-2-(4'-chlorobenzyl)-3 -isothiazolone,
4-methyl-5-chloro-2-(4'-chlorophenyl)-3-isothiazolone,
5-chloro-2-(4'- chlorobenzyl)-3-isothiazolone,
5-chloro-2-(2'-phenylethyl)-3-isothiazolone,
4,5-dichloro-2-(2'-phenylethyl)-3-isothiozolone,
4-methyl-5-chloro-2-(3', 4'-diethylbenzyl)-3-isothiazolone, and mixtures thereof.

22. The method of claim 17 wherein the leachable biocide is 4,5-dichloro-2-n-octyl-3-isothiazolone.

* * * * *